(12) United States Patent
Carnahan et al.

(10) Patent No.: US 8,908,827 B2
(45) Date of Patent: Dec. 9, 2014

(54) COMPOSITIONS, METHODS OF USE AND SYSTEMS FOR ANALYSIS OF SILICON LEVELS IN PETROLEUM MATERIALS

(75) Inventors: James Carnahan, Niskayuna, NY (US); Zewu Chen, Schenectady, NY (US); Leslie Johnson, Valatie, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 355 days.

(21) Appl. No.: 13/523,430

(22) Filed: Jun. 14, 2012

(65) Prior Publication Data

US 2012/0321045 A1    Dec. 20, 2012

Related U.S. Application Data

(60) Provisional application No. 61/498,082, filed on Jun. 17, 2011.

(51) Int. Cl.
*G01N 23/223* (2006.01)

(52) U.S. Cl.
USPC .............................. 378/47; 378/48; 378/207

(58) Field of Classification Search
CPC .......... G01N 23/223; G01N 2223/076; G01N 23/076; G01N 23/22; G01N 2223/635; A61B 6/485; A61B 6/58; A61B 6/582; A61B 6/585
USPC .............. 378/44, 45, 47, 48, 207; 252/408.1; 524/731, 860
See application file for complete search history.

*Primary Examiner* — Jurie Yun
(74) *Attorney, Agent, or Firm* — Heslin Rothenberg Farley & Mesiti P.C.

(57) ABSTRACT

This invention relates in general to the determination of silicon levels in fuel mixtures, such as petroleum products. More particularly, the present invention relates to compositions for use as standards in an x-ray analyzer for the measurement of silicon in various fuel mixtures, and to methods of using these compositions.

16 Claims, 1 Drawing Sheet

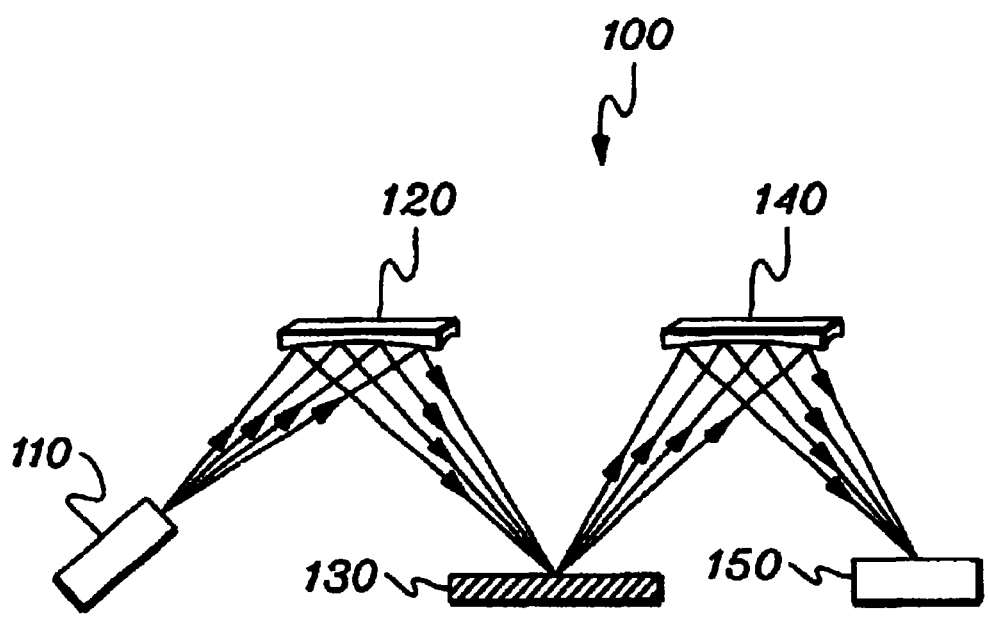

COMPOSITIONS, METHODS OF USE AND SYSTEMS FOR ANALYSIS OF SILICON LEVELS IN PETROLEUM MATERIALS

CROSS-REFERENCE TO RELATED APPLICATIONS

This application claims priority under 35 U.S.C. §119 to U.S. Provisional Application No. 61/498,082, filed Jun. 17, 2011, which is hereby incorporated by reference herein in its entirety.

TECHNICAL FIELD

This invention relates in general to the determination of silicon levels in fuel mixtures, such as petroleum products. More particularly, the present invention relates to compositions for use as standards in an x-ray analyzer for the measurement of silicon in various fuel mixtures, and to methods of using these compositions.

BACKGROUND OF THE INVENTION

There is an inherent need for fuel supplies to be as free of contaminants as possible in order to prevent unwanted effects resulting from their use. Vehicle fuels are often contaminated by silicon, and this contamination can be introduced in a number of ways. For instance, gasoline may contain toluene or other waste hydrocarbon solvents, which may contain silicon compounds. Ethanol fuel blends may become contaminated by the silicon-based antifoam agents used in ethanol plants.

The existence of silicon in fuel supplies can wreak havoc on machines and vehicles that use the fuel. The existence of silicon in gasoline, for instance, can be detrimental to certain parts of an automobile engine, including oxygen sensors, catalytic converters and spark plugs. This often leads to the unwanted cost of repairing and/or replacing these parts. In order to mitigate this damage, there is a great commercial need for a method of analyzing the amount of silicon present in petroleum products and other fuel mixtures.

SUMMARY OF THE INVENTION

The current invention in one aspect relates to a composition comprising organosiloxanes in an organic solvent. The organosiloxanes may be present in the solvent at a total concentration of about 0.5 to 3.0 wt %, and have a boiling point between 35° C. and 375° C. The organosiloxanes should be substantially free of elements other than silicon, carbon, hydrogen and oxygen. The organic solvent may have a boiling point between about 64° C. and 125° C. The organic solvent should be substantially free of elements other than carbon, hydrogen and oxygen.

The invention also relates to a method of using the composition above for calibrating an X-ray silicon analyzer by providing the composition in the X-ray silicon analyzer and measuring a response to a known concentration. The invention also relates to a system for practicing this method of calibrating an X-ray silicon analyzer.

The invention also relates to a method of using the composition above for measuring the silicon concentration in a fuel mixture. In this case, the boiling point of the composition may be matched to the boiling point of the fuel mixture to be tested. This composition is provided to calibrate an X-ray silicon analyzer. The fuel mixture to be tested is then provided to the X-ray silicon analyzer, and the concentration of the silicon in the fuel mixture is measured.

The invention also relates to a system for measuring silicon in a fuel mixture. This system includes an X-ray silicon analyzer, calibrated with a solution according to the invention. The organosiloxane contained within this solution has a boiling point matched to within the boiling point range of the fuel mixture. When the fuel mixture is provided to the X-ray silicon analyzer, the X-ray silicon analyzer measures silicon in the fuel mixture.

BRIEF DESCRIPTION OF THE DRAWINGS

FIG. 1 depicts an example of an X-ray fluorescence system that may be calibrated with compositions of the invention.

DETAILED DESCRIPTION OF THE INVENTION

In one embodiment, the invention relates to a composition comprising a solution of about 0.5% to 3.0% wt. % total of one or more organosiloxanes substantially free of elements other than silicon, oxygen, carbon and hydrogen, having a boiling point between 35° C. and 375° C., in an organic solvent having a boiling point between about 64° C. and 125° C., wherein the solvent is substantially free of elements other than oxygen, carbon and hydrogen.

Both the organosiloxanes and the solvent chosen should be X-ray stable. That is, the organosiloxanes and the solvent will not substantially decompose, degrade or evaporate when presented with X-ray or other radiation stimuli.

The organosiloxanes should be substantially volatility matched to the fuel mixture to be tested. The volatility match does not have to be exact, however. This is especially relevant when testing a fuel mixture such as gasoline. Gasoline's volatility changes with the season, with lower volatility levels in hot weather and higher volatility values in colder weather. However, octamethylcyclotetrasiloxane, with a boiling point of 175-176° C., is an appropriate organosiloxane for determining the concentration of silicon in gasoline. The person of skill performing the testing will know what the volatility of the fuel to be tested is and can ably match the organosiloxanes appropriately. One method for determining suitability includes substantially matching the boiling point value of the organosiloxanes with the range of the fuel mixture to be tested. In some embodiments of the invention, the boiling point of the organosiloxanes is substantially similar to the boiling point of the fuel mixture to be tested. In some embodiments, the organosiloxanes will have a boiling point between 35° C. and 375° C. In other embodiments, the organosiloxanes will have a boiling point between 75° C. and 200° C. In still other embodiments, the organosiloxanes will have a boiling point between 100° C. and 180° C. The testable fuel mixtures will also fall within these boiling point ranges.

The organosiloxanes used should be substantially free of elements other than silicon, oxygen, carbon and hydrogen.

In some embodiments of the invention, the organosiloxane concentration is between about 0.5% to 3.0% wt. % total. In other embodiments, the organosiloxane concentration is between about 0.5% to 2.0% wt. % total. In still other embodiments, the organosiloxane concentration is between about 0.5% to 1.5% wt. % total. In yet other embodiments, the organosiloxane concentration is between about 0.75% to 1.25% wt. % total. In other embodiments, the organosiloxane concentration is between about 0.9% to 1.1% wt. % total. In still other embodiments, the organosiloxane concentration is about 1.0% wt. % total.

Methyl-substituted organosiloxanes are particularly suitable for the compositions and methods of the invention. Suitable organosiloxanes include, but are not limited to, octamethylcyclotetrasiloxane, octamethyltrisiloxane, hexamethylcyclotrisiloxane, hexamethyltrisiloxane and hexamethyldisiloxane. The methyl cyclosiloxane oligomers with from 3 to 10 silicon units have a volatility range that covers the boiling range of gasoline and diesel fuels.

It is to be understood that various combinations of more than one of these organosiloxanes may also be used. For example, the organosiloxane present in the composition may be comprised of 98% octamethylcyclotetrasiloxane and 2% hexamethyldisiloxane. Mixtures of methyl cyclosiloxane oligomers can be made at will since the fractional silicon content of all the per-methylcyclics is the same. Thus, a distillation fraction of per-methyl cyclosiloxanes can be used without knowledge of the exact oligomer composition of the mixture.

The organic solvents for use in the invention are desirably substantially free of elements other than oxygen, carbon and hydrogen. In some embodiments, these solvents have a boiling point between about 64° C. and 125° C. In other embodiments, these solvents have a boiling point between about 75° C. and 110° C. Appropriate organic solvents for use in the invention include, but are not limited to, ethyl alcohol, toluene and isooctane, and may include ketones, higher alcohols, aromatics and/or hydrocarbons.

The fuel mixtures in which the silicon concentration may be tested include, but are not limited to, gasoline, ethanol, diesel fuel, naphthas, reformulated gasoline (RFG), jet fuels, kerosene, toluene, other related petroleum materials, biofuels and appropriate mixtures thereof. In some embodiments of the invention, the fuel mixture comprises gasoline or diesel. The volatility of the samples should be such that the light components are not lost to evaporation; it may be challenging to obtain accurate silicon readings in fuel mixtures such as light hydrocarbons or high vapor pressure gasoline.

In some embodiments, the invention relates to a composition comprising a solution of about 1.0% wt. % total of octamethylcyclotetrasiloxane and hexamethylcyclotrisiloxane in an organic solvent comprised of ethanol or toluene. For instance, octamethylcyclotetrasiloxane may comprise 98% of the organosiloxane and hexamethylcyclotrisiloxane may comprise the remaining 2%.

In some embodiments, the invention relates to a method of calibrating an X-ray silicon analyzer comprising providing a composition of the invention to the X-ray silicon analyzer and measuring the response to a known concentration of silicon. For instance, the composition may be 1.0 wt. % total of octamethylcyclotetrasiloxane and hexamethylcyclotrisiloxane in ethanol or toluene. In some embodiments, the X-ray silicon analyzer is X-Ray Optical Systems' (XOS) MWDXRF analyzer, previously disclosed.

For example, U.S. Pat. Nos. 6,934,359 and 7,072,439, hereby incorporated by reference herein in their entirety and assigned to X-Ray Optical Systems, Inc., the assignee of the present invention, disclose exemplary monochromatic wavelength dispersive x-ray fluorescence (MWD XRF) techniques and systems for the analysis of such liquid samples (e.g., petroleum products). X-ray fluorescence (XRF) is an analytical technique by which a substance is exposed to a beam of x-rays to determine, for example, the presence of certain components. The basic technique involves exciting a fuel sample with x-rays and examining the fluorescence emitted. Each element emits a unique spectral signature. A detector then measures the wavelengths of the emitted x-rays, and software can reduce this measured spectrum to a weighted composition of the sulfur in the sample.

More particularly, and with reference to FIG. 1, an XRF system 100 in accordance with the above-incorporated U.S. Patent Applications may comprise an x-ray source assembly 110, a sample chamber assembly for a sample 130 and an x-ray detector assembly 150. An x-ray optic 120 such as a curved crystal, monochromating and focusing optic may be included in the excitation path, along with another e.g., curved crystal focusing optic 140 in the detection path. The x-ray source assembly produces an x-ray beam which is focused by the x-ray focusing optic to produce a focused beam on a sample under test in a chamber assembly. The x-ray fluorescence created by the x-ray irradiation of the sample in sample excitation chamber assembly generates an x-ray fluorescent beam, which may be focused by x-ray focusing device to provide a focused x-ray beam which is directed to an x-ray detector assembly.

Such optics may broadly include, for example, curved crystal monochromating optics such as those disclosed in commonly assigned U.S. Pat. Nos. 6,285,506; 6,317,483; and 7,035,374; and/or multilayer optics; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable. Each of the above-noted patents is hereby incorporated herein by reference in its entirety.

Any of these XRF systems and/or techniques can be used in combination with the standards discussed herein, and/or for the measurement of silicon in samples, in accordance with the present invention.

In some embodiments, the invention relates to a method of measuring the presence and/or concentration of silicon in a fuel mixture. In these embodiments, the organosiloxane of the composition has a boiling point matched to the boiling point of the fuel mixture to be tested. The X-ray silicon analyzer is then calibrated with the organosiloxane composition. The fuel mixture to be tested is then provided to the X-ray silicon analyzer for testing, and the concentration of silicon in the fuel mixture is measured. In some embodiments of the invention, the composition may be 1.0 wt. % total of octamethylcyclotetrasiloxane and hexamethylcyclotrisiloxane in ethanol or toluene, and the fuel mixture is gasoline, ethanol, or diesel.

Embodiments of the invention may be used for analyzing silicon levels in hydrocarbons or biofuels in, for example, refinery laboratories, pipeline terminals, additive plants and inspection laboratories.

We claim:

1. A method of measuring silicon in a fuel mixture comprising:
   a. providing a composition comprising a solution of about 0.5% to 3.0% wt. % total of one or more organosiloxanes substantially free of elements other than silicon, oxygen, carbon and hydrogen, having a boiling point between 35° C. and 375° C., in an organic solvent having a boiling point between about 64° C. and 125° C., wherein the solvent is substantially free of elements other than oxygen, carbon and hydrogen, wherein said organosiloxane has a boiling point matched to within the boiling point range of said fuel mixture;
   b. calibrating an X-ray silicon analyzer with said solution;
   c. providing said fuel mixture to said X-ray silicon analyzer; and
   d. measuring the silicon concentration in said fuel mixture.

2. The method according to claim 1, wherein said organosiloxanes are X-ray stable.

3. The method according to claim 1, wherein said organosiloxanes are methyl-substituted siloxanes.

4. The method according to claim 3, wherein said organosiloxanes are selected from octamethylcyclotetrasiloxane, octamethyltrisiloxane, hexamethylcyclotrisiloxane, hexamethyltrisiloxane and hexamethyldisiloxane.

5. The method according to claim 1, wherein the solution contains about 1.0 wt. % organosiloxanes.

6. The method according to claim 1, wherein the organic solvent comprises ethyl alcohol, isooctane or toluene.

7. The method according to claim 1, wherein said fuel mixture comprises gasoline, ethanol, or diesel.

8. The method according to claim 1, wherein
  a. said solution comprises about 1.0 wt. % total octamethylcyclotetrasiloxane and hexamethylcyclotrisiloxane; and
  b. said organic solvent comprises ethanol or toluene.

9. A system for measuring silicon in a fuel mixture comprising:
  a. an X-ray silicon analyzer, calibrated with a composition comprising a solution of about 0.5% to 3.0% wt. % total of one or more organosiloxanes substantially free of elements other than silicon, oxygen, carbon and hydrogen, having a boiling point between 35° C. and 375° C., in an organic solvent having a boiling point between about 64° C. and 125° C., wherein the solvent is substantially free of elements other than oxygen, carbon and hydrogen, wherein said organosiloxane has a boiling point matched to within the boiling point range of said fuel mixture; and
  b. said fuel mixture, wherein the X-ray silicon analyzer measures silicon in the fuel mixture responsive to providing the fuel mixture to said X-ray silicon analyzer.

10. The system according to claim 9, wherein said organosiloxanes are X-ray stable.

11. The system according to claim 9, wherein said organosiloxanes are methyl-substituted siloxanes.

12. The system according to claim 11, wherein said organosiloxanes are selected from octamethylcyclotetrasiloxane, octamethyltrisiloxane, hexamethylcyclotrisiloxane, hexamethyltrisiloxane and hexamethyldisiloxane.

13. The system according to claim 9, wherein the solution contains about 1.0 wt. % organosiloxanes.

14. The system according to claim 9, wherein the organic solvent comprises ethyl alcohol, isooctane or toluene.

15. The system according to claim 9, wherein said fuel mixture comprises gasoline, ethanol, or diesel.

16. The system according to claim 9, wherein
  a. said solution comprises about 1.0 wt. % total octamethylcyclotetrasiloxane and hexamethylcyclotrisiloxane; and
  b. said organic solvent comprises ethanol or toluene.

* * * * *